(12) United States Patent
Basilion et al.

(10) Patent No.: US 8,454,935 B2
(45) Date of Patent: Jun. 4, 2013

(54) CELL PERMEABLE PROBE

(75) Inventors: James P. Basilion, Shaker Heights, OH (US); Jihua Hao, Beachwood, OH (US)

(73) Assignee: Case Western Reserve University, Cleveland, OH (US)

( * ) Notice: Subject to any disclaimer, the term of this patent is extended or adjusted under 35 U.S.C. 154(b) by 1196 days.

(21) Appl. No.: 11/827,666

(22) Filed: Jul. 12, 2007

(65) Prior Publication Data

US 2008/0044359 A1    Feb. 21, 2008

Related U.S. Application Data

(60) Provisional application No. 60/830,405, filed on Jul. 12, 2006.

(51) Int. Cl.
*A61K 51/00* (2006.01)
*A61M 36/14* (2006.01)

(52) U.S. Cl.
USPC ......... 424/1.69; 424/1.11; 424/1.65; 424/9.3; 424/9.361; 424/9.6; 530/328

(58) Field of Classification Search
USPC ............... 424/1.11, 1.65, 1.69, 1.81, 1.85, 424/1.89, 9.6, 9.3, 9.32, 9.36, 9.361; 534/7, 534/10–16; 530/300, 328
See application file for complete search history.

(56) References Cited

U.S. PATENT DOCUMENTS 7,807,780 B2 * 10/2010 Waugh et al. ................. 530/327

* cited by examiner

*Primary Examiner* — D L Jones
(74) *Attorney, Agent, or Firm* — Tarolli, Sundheim, Covell & Tummino LLP

(57) ABSTRACT

A cell permeable probe is disclosed. The cell permeable probe includes a cell membrane translocating element, which facilitates transport of the probe into the intracellular component of a cell. The cell permeable probe may also include a plurality of binding moieties for a disease specific marker and a contrast agent.

9 Claims, 7 Drawing Sheets

Figure 4

CELL PERMEABLE PROBE

CROSS REFERENCE TO RELATED APPLICATION

This application claims the benefit of U.S. Provisional Application 60/830,405 filed Jul. 12, 2006, titled Cell Permeable Probe, by the same inventors.

COPYRIGHT NOTICE

A portion of the disclosure of this patent document contains material that is subject to copyright protection. The copyright owner has no objection to the facsimile reproduction of the patent document or the patent disclosure as it appears in the Patent and Trademark Office patent file or records, but otherwise reserves all copyright rights whatsoever.

BACKGROUND

Early cancer diagnosis is an ongoing challenge. Some conventional diagnosis techniques involve intracellular probing methods. These conventional methods may rely on accumulation of an intracellular probe to allow differentiation of diseased cells from non-diseased cells. Probe accumulation may provide for enhanced contrast between cells as a result of probe cleavage. This approach may result in non-specific contrast between cells. Conventional methods may utilize one binding moiety specific to a disease marker to retain a contrasting agent in the intracellular compartment. This approach may be insensitive to small differences between disease markers in diseased cells and non-diseased cells.

DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

FIG. 4 illustrates a mechanism for chemical synthesis of a cell permeable probe with a plurality of binding moieties for a disease-specific marker.

DETAILED DESCRIPTION

Figure 1:
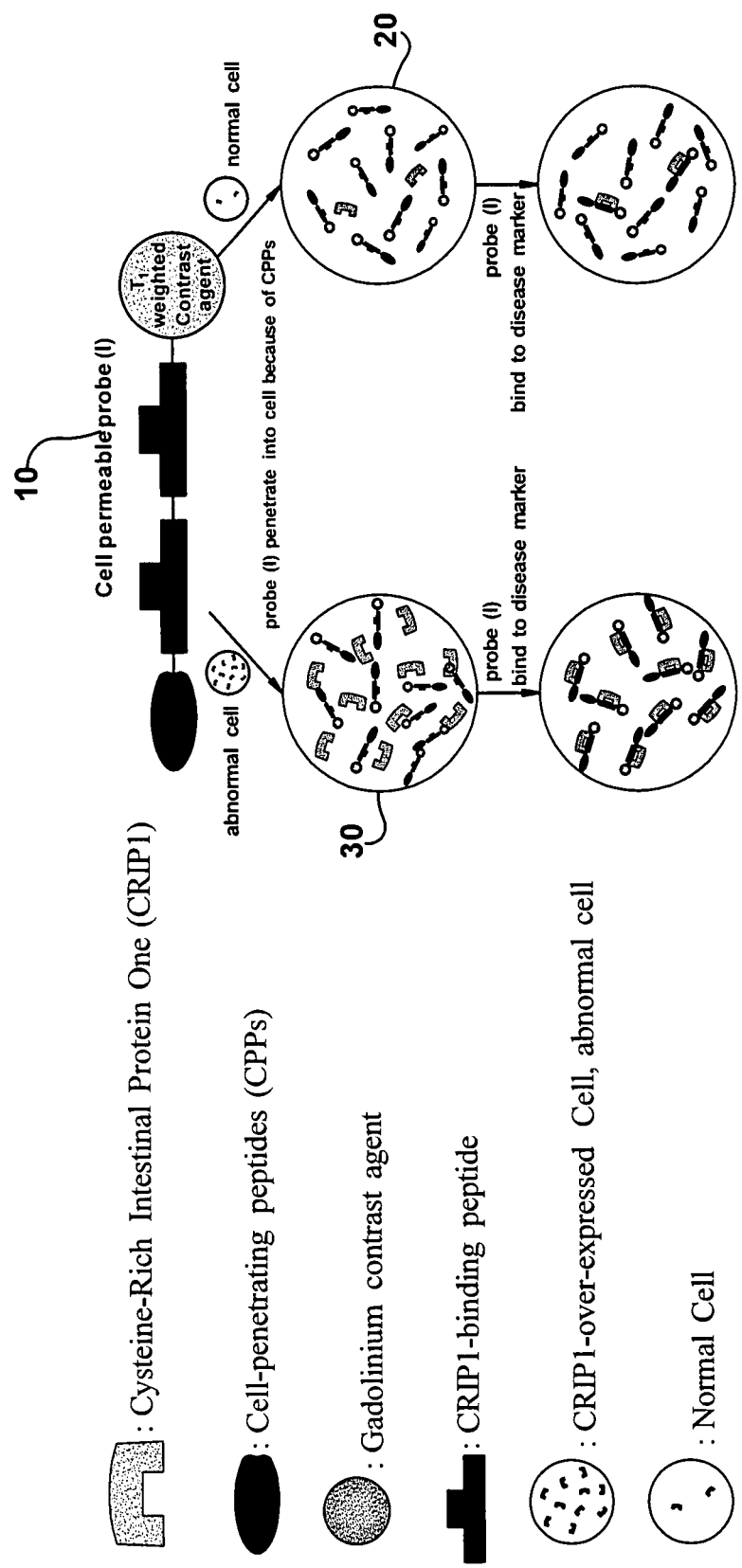
FIG. 1 illustrates an example cell permeable probe interacting with a normal cell and a cell in which an over-expressed molecular marker appears.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Intracellular disease marker", as used herein, refers to an over-expressed molecular marker in the intracellular space of a diseased cell relative to expression of the molecular marker in the intracellular space of a normal cell. In one example, the disease marker may be a protein over-expressed in a cancer cell. In another example, the disease marker may be a mRNA over-expressed in a breast cancer cell.

"Logic", as used herein, includes but is not limited to hardware, firmware, software in execution and/or combinations thereof to perform a function(s) or an action(s), and/or to cause a function or action from another logic, method, and/or system. Logic may include a software controlled microprocessor, discrete logic (e.g., application specific integrated circuit (ASIC)), an analog circuit, a digital circuit, a programmed logic device, a memory device containing instructions, and so on. Logic may include a gate(s), a combinations of gates, other circuit components, and so on. Where multiple logical logics are described, it may be possible in some examples to incorporate the multiple logical logics into one physical logic. Similarly, where a single logical logic is described, it may be possible in some examples to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

Example systems and methods described herein concern a cell permeable probe that may be used in MRI (magnetic resonance imaging) applications. The probe may be, for example, a T1-weighted probe. The T1-weighted probe may interact with intracellular targets (e.g., markers) rather than extracellular targets. An example T1-weighted probe may include a plurality of binding moieties (e.g., chemical molecules) specific to an intracellular disease marker, a cell membrane translocating element (e.g., cationic peptide (Tat peptide), FGF (fibroblast growth factor), AntpHD, penatratin), and a T1-weighted contrast agent (e.g., $Gd^{3+}$). The contrast agent may be carried into a cell by the cell membrane translocating element and then either remain in or exit the cell based on interactions between the plurality of binding moieties and the intracellular disease markers. When the cell permeable probe remains bound to an intracellular disease marker, the T1-weighted contrast agent may be retained in the intracellular space of a cell. Retention of the T1-weighted contrast agent in the intracellular space may facilitate enhancing MR images by, for example, enhancing contrast between normal cells and diseased cells. Retention of the T1-weighted contrast agent in the intracellular space may also facilitate increased MRI sensitivity for disease detection. The binding of the probe to the disease marker may lead to changes, for example, in T1 relaxivity of a cell. In one example, the high molecular weight of the cell permeable probe may facilitate the change in T1 relaxivity of a cell. This change in relaxivity facilitates acquiring images in which diseased cells are differentiated from normal cells. This change in T1 relaxivity may also facilitate increased MR sensitivity for disease detection. These images may then be used, for example, to plan and/or evaluate surgery, to plan and/or evaluate radiation therapy, to plan and/or evaluate radio surgery, to plan and/or evaluate chemical therapeutics, to plan and/or evaluate chemotherapy, and so on.

Example probes may be used in diagnostics and/or screening. In one example, a probe may be used for cancer screening where a marker indicates that a tissue is going to become malignant but has not yet become malignant. Thus, in one example, the intracellular disease marker may be a pre-malignancy marker and/or an early-stage malignancy marker.

One example method facilitates in vivo MR imaging of changes in gene expression between normal and diseased cells. The probe includes an element for membrane translocation, elements for targeting specific disease markers, and a T1-weighted contrast element. While a T1-weighted contrast element is described, it is to be appreciated that other contrast agents (e.g., T2-weighted contrast element, PARACEST agent) could be employed. While separate membrane translocation elements and binding moieties are described, it is to be appreciated that a single molecule may perform both these actions.

The cell membrane translocating element may include, for example, cell penetrating peptides, small molecules, ligands to internalizing cell surface receptors, and so on. In one example, the cell translocating element may be a Tat peptide. A T1-weighted contrast agent may be a multi composite T1-weighted contrast agent and may include multiple-binding sites to a disease marker.

In one example, a cell permeable probe facilitates enhancing contrast during MR imaging between a normal cell and a cell over-expressing cysteine-rich intestinal protein 1 (CRIP1). CRIP1 has been identified as a biomarker for human breast cancers, cervical cancers, and pancreatic cancers. CRIP1 mRNA is over-expressed 8-10 fold in 90% of invasive and ductal carcinoma in situ breast cancers. A correlation between CRIP1 protein expression and CRIP1 mRNA expression has been demonstrated. CRIP1 protein was measured by Western blot and CRIP1 mRNA was measured by Q-RT-PCR. Therefore, in one example, a cell permeable probe specific to CRIP1 protein may be used as an early diagnostic tool for breast cancer. The example probe relies on the receptor-induced magnetization enhancement (RIME) principle whereby a cell permeable probe penetrates a cell and binds to a CRIP1 protein. The binding of the probe to the protein changes T1 relaxivity of the probe associated with the target in the cell. In other examples, cells that do not express the disease marker may still contain the probe, however the probe will not exhibit the change in relaxivity that occurs when the probe binds to the disease marker. The motion of the probe is limited when bound to the protein, which leads to a change in T1 relaxivity which in turn increases MR signal differentiation. Since the probe includes a plurality of binding moieties specific to a chosen intracellular marker (e.g., disease marker), the concentration of bound contrast agent will be higher in a cell over-expressing the disease marker than in a normal cell. Thus, the intracellular probe facilitates differentiating between normal and diseased cells using MRI.

FIG. 1 illustrates an example cell permeable probe 10 interacting with a normal cell 20 and a diseased cell 30 in which an over-expressed molecular marker appears. The cell permeable probe 10 penetrates the cells and binds to CRIP1. In the diseased cell 30, CRIP1 is over-expressed, so more probe binding occurs than does in the normal cell. The specific probe binding causes a high retention of the cell permeable probe within the intracellular space. The diseased cell 30 therefore contains more contrast agent than the normal cell 20 and thus its signal intensity increases. In addition, a probe that is bound to an intracellular disease marker has increased relaxivity. These two phenomena cause a detectable change in signal using MRI. This may facilitate acquiring MR images where normal and diseased cells are differentiated. While CRIP1 and T1-weighting are described, it is to be appreciated that other disease markers and other contrast agents may be employed.

Figure 2:
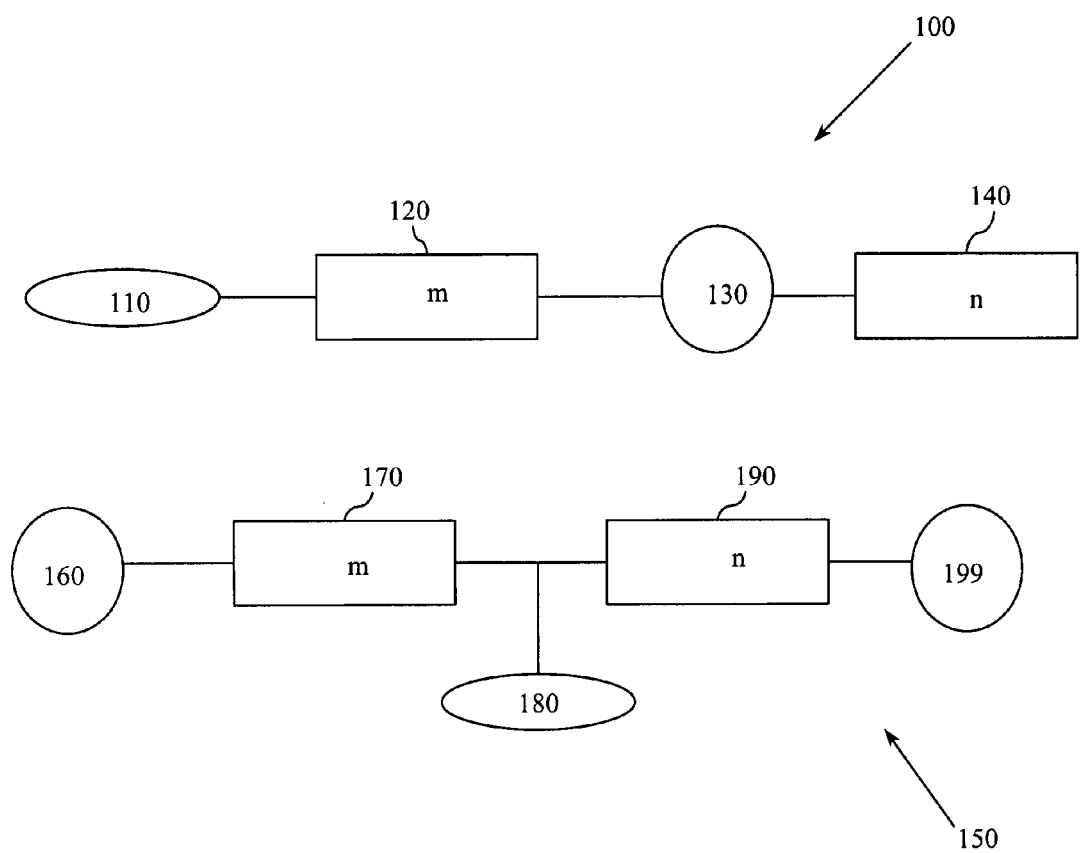
FIG. 2 illustrates different example architectures for cell permeable probes.

FIG. 2 illustrates different architectures for example probes. While two different configurations are presented, it is to be appreciated that other configurations may be employed. Other architectures may also include, for example, linker molecules. The example architectures are intended to illustrate that a probe can incorporate its various elements at various sites. For example, a probe may include various binding elements at various sites, may include various contrast elements at various sites, and may include various cell translocating elements at various sites. In one example, the cell permeable probe may have multiple binding moieties where each binding moiety is a different small chemical molecule. It is to be appreciated that the cell translocating elements may include, for example, cell penetrating peptides or other cell penetrating molecules including a ligand for an internalizing receptor, or a small molecule. Additionally, a binding moiety may also possess cell translocating characteristics.

In one example, a cell permeable probe 100 may have a translocating element 110, two binding moieties (120,140) specific to a disease marker and a contrast agent 130. For elements 120 and 140 m and n represent numbers indicating that probe 100 may include m and/or n binding moieties. In another example, the cell permeable probe 150 may have a translocating element 180, two contrast agents (160, 199) and two binding moieties (170, 190) specific to a disease marker. For elements 170 and 190 m and n represent a number.

In one example, a cell permeable probe may be employed to uncover informative molecular markers for in vitro and/or in vivo tissue identification. For example, CRIP1, which is implicated in breast cancer, may be a target for a binding moiety of a cell permeable probe. Thus, after application of the probe, breast cancer cells may be imaged using MRI. The breast cancer cells that take up the probe and in which the contrast agent is subsequently captured may produce a more intense MR signal than is conventional.

Figure 3:
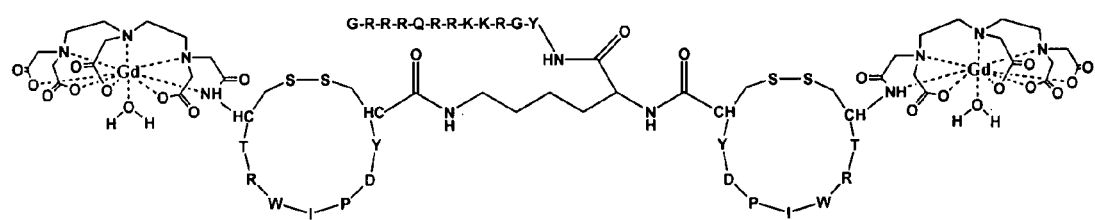
FIG. 3 illustrates a chemical structure for one example cell permeable probe.

FIG. 3 illustrates a chemical structure for an example cell permeable probe. The example may facilitate imaging increased CRIP1 expression associated with disease through MRI. The plurality of binding sites may cause a high retention of the contrasting agent in the intracellular space allowing differentiation between diseased and normal cells.

In this example the probe may be a bioconjugate that includes a Tat peptide with a sequence of Y-G-R-K-K-R-R-Q-R-R-R (SEQ NO. 3), disulfide linked cyclic peptides each with two terminal cysteines, a plurality of binding moeities with sequences C-Y-D-P-I-W-R-T-C (SEQ NO. 1), and a T1-weighted contrast agent Gd-DTPA chelate. While a Tat peptide sequence and a binding moiety sequence are listed, it is to be appreciated that other sequences with similar properties can be employed. When the example probe is delivered into the cell by the Tat peptide, it will bind to CRIP1 located in the intracellular space of a cell. Upon binding, an MR signal from diseased cells will change relative to normal cells due to the increased level of CRIP1 protein expression. The increased CRIP1 protein expression provides greater contrast between normal and diseased cells in MR images.

Figure 4:
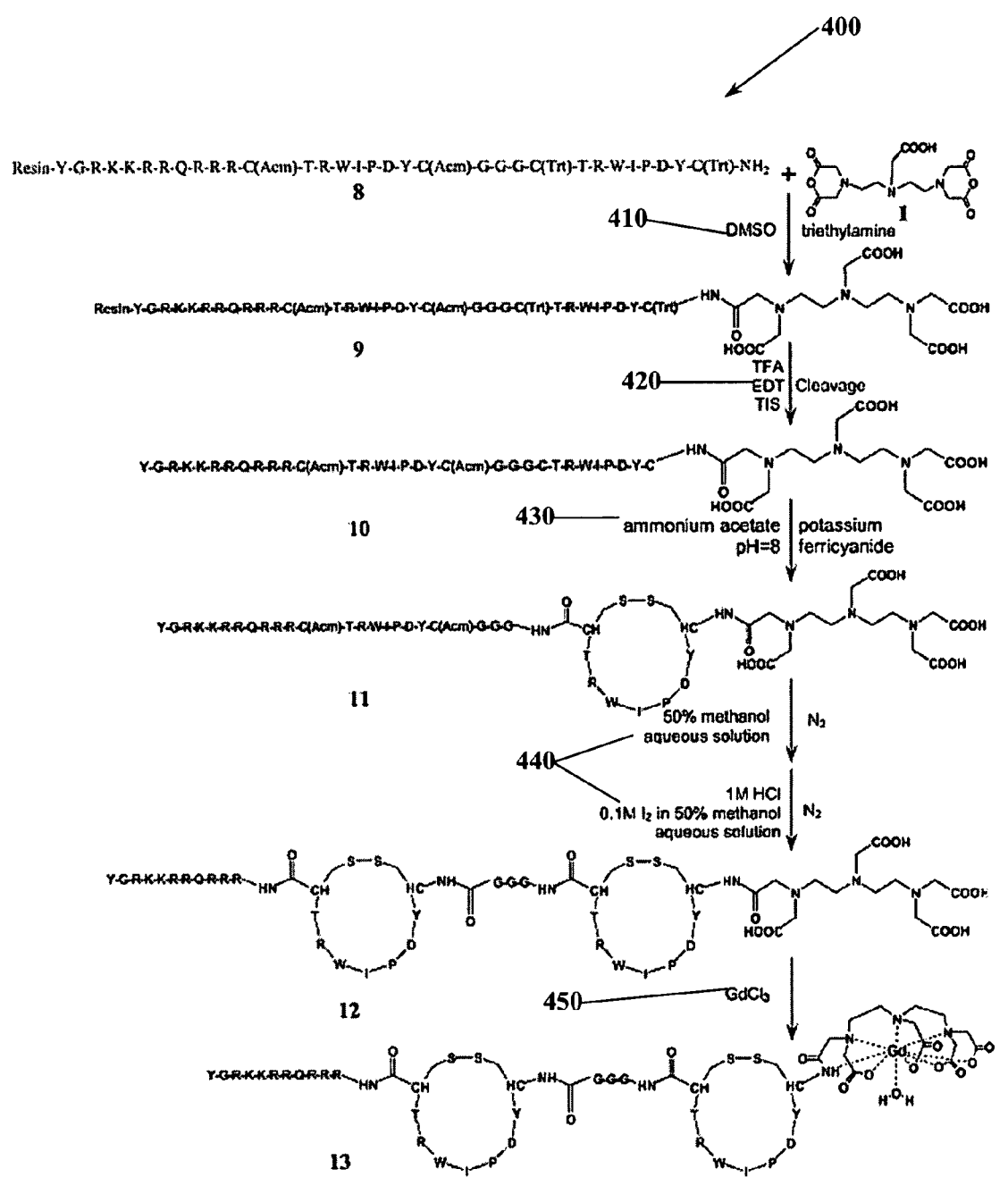

FIG. 4 illustrates a mechanism 400 for chemical synthesis of a cell permeable probe with a plurality of binding moieties for a disease-specific marker. The cell permeable probe is synthesized with one translocating element, two circularized disease specific binding moieties and one signaling agent.

Example methods may be better appreciated with reference to flow diagrams. While for purposes of simplicity of explanation, the illustrated methods are shown and described as a series of blocks, it is to be appreciated that the methods are not limited by the order of the blocks, as in different embodiments some blocks may occur in different orders and/or concurrently with other blocks from that shown and described. Moreover, less than all the illustrated blocks may be required to implement an example method. While the figures illustrate various actions occurring in serial, it is to be appreciated that in some examples various actions could occur concurrently, substantially in parallel, and/or at substantially different points in time.

Figure 5:
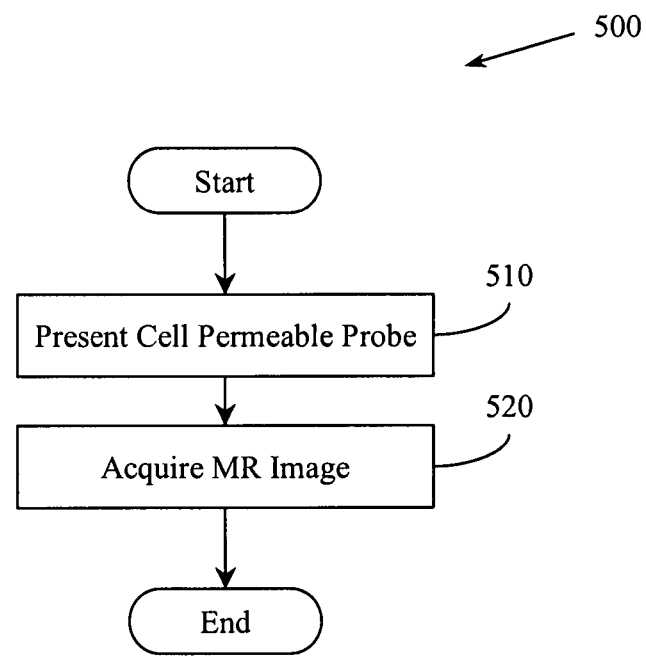
FIG. 5 illustrates a method associated with imaging a cell that is interacting with a cell permeable probe.

FIG. 5 illustrates a method 500 associated with imaging a cell interacting with a cell permeable probe. Method 500 may include, at 510, presenting a cell permeable probe to a tissue. Presenting the cell permeable probe may include, for example, intravenously introducing the probe to a patient, intraperioneally introducing the probe to a patient, topically applying the probe, and so on. Method 500 may also include, at 520, acquiring an MR image of the tissue. Method 500 may also include, planning a radiologic therapy based on the MR image, guiding a surgeon based on the MR image, and/or guiding a surgical apparatus based on the MR image.

Figure 6:
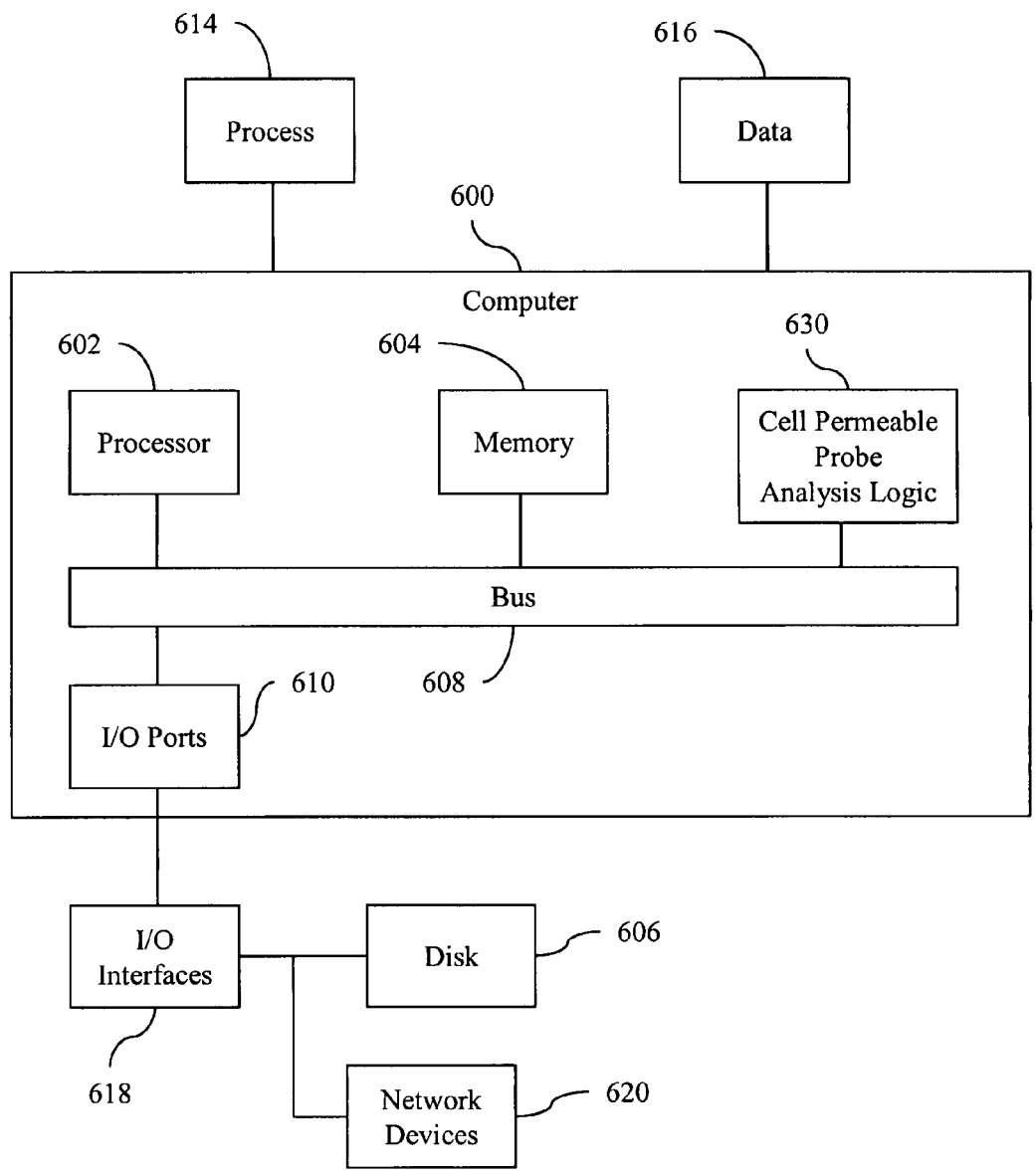
FIG. 6 illustrates an example computing environment with which example systems and methods illustrated herein may operate.

FIG. 6 illustrates an example computing device with which example systems and methods described herein, and equivalents, may operate. The example computing device may be a computer 600 that includes a processor 602, a memory 604, and input/output ports 610 operably connected by a bus 608. In one example, the computer 600 may include a cell permeable probe analysis logic 630 to facilitate identifying cells in which a contrast agent has bound after being carried into the cell. In different examples, the logic 630 may be implemented in hardware, software, firmware, and/or combinations thereof. Thus, the logic 630 may provide means (e.g., hardware, software, firmware) for identifying cells, for planning a radiologic therapy, for guiding a surgical device, and so on. While the logic 630 is illustrated as a hardware component attached to the bus 608, it is to be appreciated that in one example, the logic 630 could be implemented in the processor 602.

Generally describing an example configuration of the computer 600, the processor 602 may be a variety of various processors including dual microprocessor and other multi-processor architectures. A memory 604 may include volatile memory and/or non-volatile memory.

A disk 606 may be operably connected to the computer 600 via, for example, an input/output interface (e.g., card, device) 618 and an input/output port 610. The disk 606 may be, for example, a magnetic disk drive, a solid state disk drive, a floppy disk drive, a tape drive, a Zip drive, a flash memory card, and/or a memory stick. Furthermore, the disk 606 may be a CD-ROM, a CD recordable drive (CD-R drive), a CD rewriteable drive (CD-RW drive), and/or a digital video ROM drive (DVD ROM). The memory 604 can store a process 614 and/or a data 616, for example. The disk 606 and/or the memory 604 can store an operating system that controls and allocates resources of the computer 600.

The bus 608 may be a single internal bus interconnect architecture and/or other bus or mesh architectures. While a single bus is illustrated, it is to be appreciated that the computer 600 may communicate with various devices, logics, and peripherals using other busses (e.g., PCIE, SATA, Infiniband, 1394, USB, Ethernet). The bus 608 can be types including, for example, a memory bus, a memory controller, a peripheral bus, an external bus, a crossbar switch, and/or a local bus.

The computer 600 may interact with input/output devices via the i/o interfaces 618 and the input/output ports 610. Input/output devices may be, for example, a keyboard, a microphone, a pointing and selection device, cameras, video cards, displays, the disk 606, the network devices 620, and so on. The input/output ports 610 may include, for example, serial ports, parallel ports, and USB ports.

The computer 600 can operate in a network environment and thus may be connected to the network devices 620 via the i/o interfaces 618, and/or the i/o ports 610. Through the network devices 620, the computer 600 may interact with a network. Through the network, the computer 600 may be logically connected to remote computers. Networks with which the computer 600 may interact include, but are not limited to, a local area network (LAN), a wide area network (WAN), and other networks.

Figure 7:
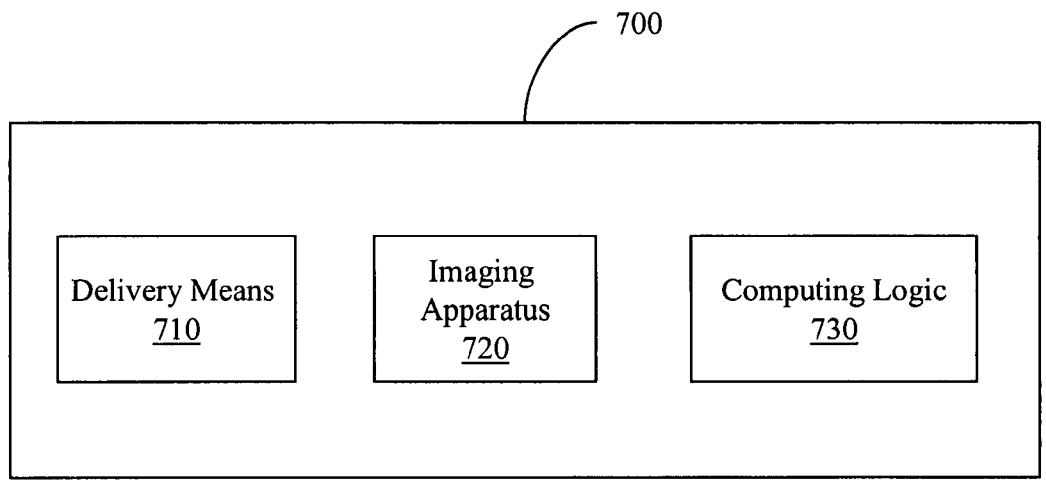
FIG. 7 illustrates an example system associated with imaging a cell that is interacting with a cell permeable probe.

FIG. 7 illustrates a system 700 that is associated with imaging a cell that is interacting with a cell permeable probe. System 700 may include means 710 for delivering a cell permeable probe to a tissue. These means may include, for example, an intravenous delivery system, a topical delivery system, an inhalation delivery system, and so on. System 700 may also include an imaging apparatus 720 to acquire an image from the tissue. The image is contrast enhanced based, at least in part, on the interaction of the cell permeable probe with an intracellular disease marker. The imaging apparatus 720 may be, for example, an MR apparatus. System 700 may also include a computing logic 730 to analyze the image. Computing logic 730 may be, for example, a standalone computer, a network computer, a logic(s) embedded in imaging apparatus 720, and so on. Computing logic 730 may facilitate, for example, identifying diseased cells, preparing a radiologic therapy to treat the diseased cells, guiding a surgeon or surgical device, and so on.

EXAMPLES

The following examples are provided to illustrate the methods of aspects of the invention, and are not to be construed as limiting the invention in any manner.

Example 1

Expression and Purification of CRIP1 Protein

The coding region of the CRIP1 cDNA was amplified using primers designed to add a 5'-BamH I restriction site, stop codons and an EcoR I site at the 3'-end of the approximately 250 base pair amplification product. The PCR products were gel purified and cloned into the BamHI/EcoRI sites of the vector pHAT10 (BD Clontech) and transformed into the *E. coli* strain XL1-Blue (Stratagene). To isolate the affinity-tagged recombinant protein, cultures of the cells expressing the construct were induced with IPTG, harvested, resuspended in purification buffer with 0.75 mg/ml lysozyme and PMSF. Following sonication, the lysates were cleared by centrifugation, and incubated with TALCON CellThru resin. The tagged protein was eluted from the washed column with imidizole in Extraction/Wash Buffer, yielding approximately 1 mg of recombinant protein per liter of culture.

Example 2

Phage Display Studies

CRIP1 was digested with enterokinase to remove the His tag. The cleaved tag was removed by incubation with TALON resin. The purified CRIP1 was used for four rounds of panning with the PhD.-C7C Phage Display Peptide Library (New England Biolabs) to identify peptides that bind to CRIP1 protein with a high affinity. To reveal peptide sequences the isolated CRIP1 binding phage were amplified and subjected to sequencing across the region that codes for the C7C peptide.

Example 3

Phage Binding and Affinity

The affinity of the phage clones for purified CRIP1 was assessed as follows. Increasing log concentrations of phage were incubated with a constant concentration of protein immobilized on immuno plates. After incubation and washing, phage were eluted with an acidified buffer and quantified by counting plaque-forming units.

Example 4

CRIP1 Peptide Synthesis and Binding Studies

Initial binding studies were conducted with isolated phage to determine which phage contain the peptides of highest affinity for CRIP1. Peptides from the highest affinity phage were synthesized, circularized and labeled at the C-terminal end with 5-FAM. The peptides were synthesized on a Peptide Synthesizer 433A (Applied Biosystems) using Fmoc chemistry protocols with HBTU activation. The affinity of the peptide for the purified CRIP1 protein was determined by saturation binding experiments. 96 well plates were coated with 150 µl of PBS buffer containing 100 µg/ml of CRIP1 protein and incubated overnight at 4° C. Each well was washed with TBS buffer containing 0.1% Tween-20 (TBST) and then filled with blocking buffer and incubated for one hour. Following the one-hour incubation the wells were washed six times with TBST. Then 100 µl of binding buffer containing 5-Fam circularized peptides was added and incubated for one hour at 37° C. Following incubation the plates were washed with binding buffer and the fluorescence intensity was determined.

Example 5

Translocating Peptide Synthesis

5-Fam-labeled Tat peptides were synthesized on Wang resin using solid phase synthesis on an automatic peptide synthesizer. 5-Fam was activated by HBTU/HOBT and coupled to the N-terminal on the peptide. The peptide was treated with trifluoroacetic acid. The peptide was purified by reversed-phase high-pressure liquid chromatography.

Example 6

Localization of Translocating Peptide in Breast Cancer Cells

To determine the membrane permeability of the Tat peptide in MCF-7 and MCF-10A, the cells were incubated for six hours in medium containing 100 µM 5-Fam-labeled Tat peptide.

Example 7

Cell Permeable Probe Synthesis

The peptide will be synthesized on a Peptide Synthesizer 433A using Fmoc chemistry protocols with HBTU activation. The starting resin will be Fmoc-Rink-Amide resin or Fmoc-knorr Amide Resin. All amino acids will have standard side chain protecting groups except for the C-terminal lysine residue, which will contain a (4,4-dimethyl-2,6-dioxocyclohex-1-ylidene) ethyl (Dde) functionality protecting the ϵ-amino group to allow orthogonal synthesis by selective deprotection of the Dde while the peptide is attached to the resin. After completion of the synthesis, the peptide resin will be washed with DIPEA and DCM and kept dry for the next reaction.

DTPA will be added to the N-terminal residue by dissolving DTPA in DMSO and reacting the DTPA solution with the peptide resin 410. The coupling of DTPA will be allowed to proceed for 24 hours at room temperature. The peptide-DTPA on resin will be washed with DMSO, DMF, methanol, DCM and kept dry for the next reaction.

The peptide-DTPA will be cleaved from the resin support using 2.5% EDT, 1% TIS, 94.5% TFA and 2% water for 2 hours at room temperature and then precipitated in ether 420. The peptide-DTPA will then be purified by reverse phase HPLC on a 90A Proteo Jupiter column using a gradient system of 0.1% aqueous TFA containing 4% acetonitrile. The resulting product from the previous step will be placed in a flask and treated with ammonium acetate and potassium ferricyanide 430.

The peptide-DTPA will be dissolved in 50% aqueous methanol solution under $N_2$ 440. 1M HCl will then be added to the above solution and followed immediately by an addition of 0.1 M $I_2$ in 50% aqueous methanol solution 440. After 30 minutes of vigorous stirring, the iodine will be quenched by adding 1 M aqueous sodium thiosulfate drop-wise until the mixture is colorless and concentrated by evaporation under reduced pressure to approximately one third of the solution. The solution will be purified by reverse phase HPLC on a 90A Proteo Jupiter column using a linear gradient system of 0.1% aqueous TFA and 0.1% TFA in acetonitrile.

GdCl3 in water will be added drop wise into cyclic peptide-DTPA 450. After one hour, the solution will be purified by reverse phase HPLC on a 90A Proteo Jupiter column using a linear gradient system of 0.1% aqueous TFA and 0.1TFA in acetonitrile.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A cell permeable probe, comprising:
a cell membrane translocating element;
a plurality of binding moieties that bind to CRIP-1 protein, the binding moieties comprising peptides that include the amino acid sequence of SEQ ID NO: 1; and
a T1-weighted contrast agent;
where the cell membrane translocating element facilitates transporting the probe into the intracellular component of a cell, and wherein binding of the probe to CRIP-1 protein facilitates a detectable change in relaxivity of the T1-weighted contrast agent.

2. The probe of claim 1, wherein the contrast agent is Gd-DTPA chelate or Gd-DOTA.

3. The probe of claim 1, the contrast agent further including a T2-weighted contrast agent.

4. The probe of claim 1, the contrast agent is a PARACEST agent.

5. The probe of claim 1, the cell membrane translocating element is a ligand that is internalized to the intracellular compartment through a cell surface receptor.

6. The probe of claim 1, the cell membrane translocating element is a cationic peptide.

7. The probe of claim 1, the cell membrane translocating element is selected from the group consisting of a Tat peptide, a fibroblast growth factor, AntpHD, and penatratin.

8. The probe of claim 1, the cell membrane translocating element comprising the amino acid sequence SEQ NO 3.

9. A cell permeable probe, comprising:
a cell membrane translocating element;
a plurality of binding moieties comprising the amino acid sequence SEQ NO 1; and
a contrast agent;

---

SEQUENCE LISTING

<160> NUMBER OF SEQ ID NOS: 3

<210> SEQ ID NO 1
<211> LENGTH: 9
<212> TYPE: PRT
<213> ORGANISM: Homo sapiens

<400> SEQUENCE: 1

Cys Tyr Asp Pro Ile Trp Arg Thr Cys
1               5

<210> SEQ ID NO 2
<211> LENGTH: 9
<212> TYPE: PRT
<213> ORGANISM: Homo sapiens

<400> SEQUENCE: 2

Cys Leu Lys Asp Asn His Arg Ser Cys
1               5

<210> SEQ ID NO 3
<211> LENGTH: 11
<212> TYPE: PRT
<213> ORGANISM: Homo sapiens

<400> SEQUENCE: 3

Tyr Gly Arg Lys Lys Arg Arg Gln Arg Arg
1               5                   10 where the cell membrane translocating element facilitates transporting of the probe into the intracellular component of a cell, and where the plurality of binding moieties facilitate binding the probe to an intracellular molecular marker.

* * * * *